(12) United States Patent
Gellert et al.

(10) Patent No.: US 6,454,840 B1
(45) Date of Patent: Sep. 24, 2002

(54) SEPARATION-COLUMN UNIT FOR A GAS-CHROMATOGRAPH AND METHOD FOR MAKING THE SAME

(75) Inventors: Udo Gellert, Bellheim; Friedhelm Müller, Linkenheim-Hochstetten; Arno Steckenborn, Berlin, all of (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 09/763,157
(22) PCT Filed: Aug. 18, 1999
(86) PCT No.: PCT/DE99/02597
§ 371 (c)(1), (2), (4) Date: May 1, 2001
(87) PCT Pub. No.: WO00/11477
PCT Pub. Date: Mar. 2, 2000

(30) Foreign Application Priority Data

Aug. 20, 1998 (DE) .......................... 198 37 882

(51) Int. Cl.[7] .............................................. B01D 15/08
(52) U.S. Cl. ............................ 96/101; 95/82; 55/DIG. 5
(58) Field of Search ................. 95/82–89; 96/101–109; 55/524, DIG. 5

(56) References Cited

U.S. PATENT DOCUMENTS

| | | | | |
|---|---|---|---|---|
| 3,149,941 A | * | 9/1964 | Barnitz et al. ................. | 96/101 |
| 3,254,479 A | * | 6/1966 | Goeschl ........................ | 96/104 |
| 3,477,207 A | * | 11/1969 | Auger .......................... | 96/104 |
| 3,630,006 A | * | 12/1971 | Sandoval ...................... | 96/101 |
| 4,116,836 A | * | 9/1978 | DeAngelis ................. | 96/106 X |
| 4,891,120 A | | 1/1990 | Sethi et al. ............. | 204/299 R |
| 4,935,040 A | * | 6/1990 | Goedert ...................... | 96/104 X |
| 5,116,495 A | | 5/1992 | Prohaska ................. | 210/198.2 |
| 5,132,012 A | * | 7/1992 | Miura et al. ............. | 96/101 X |
| 5,165,292 A | * | 11/1992 | Prohaska ................... | 96/102 X |
| 5,575,929 A | | 11/1996 | Yu et al. ....................... | 216/10 |
| 5,583,281 A | | 12/1996 | Yu ............................ | 73/23.42 |
| 5,658,413 A | * | 8/1997 | Kaltenbach et al. ......... | 95/82 X |
| 6,296,685 B1 | * | 10/2001 | Cammann et al. .......... | 95/82 X |

FOREIGN PATENT DOCUMENTS

| | | |
|---|---|---|
| EP | A1750190 | 12/1996 |
| WO | A1-9728490 | 8/1997 |
| WO | A1-9854568 | 12/1998 |

* cited by examiner

*Primary Examiner*—Robert H. Spitzer
(74) *Attorney, Agent, or Firm*—Harness Dickey & Pierce PLC

(57) ABSTRACT

A separation-column unit includes a support plate having a groove formed therein on one side and running, for example, in the form of a spiral, and having a cover plate which bears against this side. In order to achieve the high separation capacity combined with a high load-bearing capacity with regard to the amount of sample flowing through, the depth (d) of the groove is preferably at least three times greater than its width. The base of the groove preferably has a rounded cross section, it being possible for the cover plate to contain a corresponding channel.

40 Claims, 3 Drawing Sheets

SEPARATION-COLUMN UNIT FOR A GAS-CHROMATOGRAPH AND METHOD FOR MAKING THE SAME

This application is the national phase under 35 U.S.C. §371 of PCT International Application No. PCT/DE99/02597 which has an International filing date of Aug. 18, 1999, which designated the United States of America.

FIELD OF THE INVENTION

The invention relates to a separation-column unit for a gas chromatograph, having a support plate, which on one side contains a groove which runs in a predetermined continuous line and on this side is covered by a cover plate. The invention also relates to a process for producing a separation-column unit of this type.

BACKGROUND OF THE INVENTION

A separation-column unit of this type is known from U.S. Pat. No. 5,583,281. The production of this separation-column unit is described in U.S. Pat. No. 5,575,929. In this process, a groove which runs in the shape of a spiral and is of semicircular cross section is formed in a support plate made from silicon by isotropic etching. In the same way, a channel, which is likewise semicircular in cross section, is etched into a cover plate. Then, the two plates are connected to one another, the groove in the support plate and the channel in the cover plate complementing one another to form a spiral-shaped capillary which is circular in cross section. On the inside, the capillary can be coated in a known way with a separation phase, in order to form the separation column.

In practice, however, separation columns are designed as glass capillaries which are round in cross section and the inner surface of which is coated with the separation phase. For economic reasons, there is no particular sense in designing such separation columns as a unit comprising a support plate and cover plate, since, apart from resulting in a smaller structure, this does not lead to any discernible technical benefits. Rather, the separating capacity of the separation column may be reduced considerably if, on account of geometric flaws, the groove in the support plate and the channel in the cover plate are not precisely congruent and therefore the cross section of the capillary formed is not circular.

Separation columns with a very small internal diameter of the capillary, which are known as narrow-bore columns, are distinguished by a high separation capacity, the optimum level of which is reached at a defined velocity of the sample flowing through the separation column. A further advantage of such separation columns is that at higher flow velocities of the sample, the separation capacity is reduced only slightly. As such, the analysis time can be shortened drastically without a significant deterioration in the separation capacity. This is of great importance in particular for on-line chromatography, on account of it being directly incorporated in the industrial control process. By contrast, a drawback is the low load from the amount of sample to be separated which these narrow-bore columns are able to bear. This is because, if the amounts of sample increase the separation phase rapidly becomes overloaded, there is an enormous deterioration in the separation capacity.

SUMMARY OF THE INVENTION

The invention is therefore based on the object of providing a separation column which is distinguished both by a high separating capacity—even at relatively high flow velocities of the sample—and by a high load-bearing capacity with regard to the amount of sample.

According to the invention, the object is achieved by the fact that, with the separation-column unit described in the introduction or the process for its production, the depth of the groove is or is designed to be greater than its width. As a result, the surface area of the separation column which is active in the chromatographic separation is enlarged with respect to its volume, so that both the separation capacity and the load-bearing capacity of the separation-column unit are improved. Because of this it is possible, for example for a given separation capacity, to reduce the length of the separation column compared to conventional separation columns which are circular in cross section, so that the overall size of the separation-column unit can be reduced accordingly.

Although it is conceivable for the glass capillary in conventional separation columns to be compressed by pressing or rolling, in order in this way to produce an elongate cross section, the cross section which is produced in this process varies over its length. This is because the compression in the center of the cross section is greater than at the ends of the cross section, on account of the resistance to deformation being lower in the center. Consequently, the flow velocity of the sample and therefore the chromatographic separation vary over the length of the cross section. Thus, the so-called peak, which is recorded at the exit from the separation column as a curve illustrating the concentration of that component of the sample, which is to be detected over time, becomes wider, thereby reducing the separation capacity. Since, in the separation-column unit according to the invention, the groove, which forms the separation column is not formed by material deformation, but rather by removal of material, it is possible to attain a cross section of the separation column which is particularly uniform over the depth of the groove, i.e. the length of the cross section. The results is that the theoretically elevated separation capacity is also achieved in practice.

It is also known to increase the load-bearing capacity of a separation-column unit while maintaining a constantly high separation capacity by connecting a plurality of conventional separation columns of small diameter in parallel. In this case, however, the problem arises that if the distribution of the sample stream to the individual separation columns is not completely uniform and if there are very minor changes in the diameter and in the coating of the separation columns, the peaks have different running times. The different running times, after they have been brought together at the outlet from the separation-column unit, widen the total peak and therefore reduce the separation capacity. By contrast, in the separation column unit according to the invention, the precise production and coating options which are specified in more detail below allow much higher separation capacities to be achieved while maintaining the high load-bearing capacity.

In the separation-column unit according to the invention, the depth of the groove is preferably at least three times greater than its width, the width lying in a range between 100 and 150 $\mu$m and the depth lying in a range from 500 to 600 $\mu$m.

In order to achieve a uniform velocity distribution of the sample flowing through the separation column even in the region of the base, the groove preferably has a rounded, in particular semicircular cross section in that region. For the same reason, the cover plate may, on its side facing toward the support plate, contain a channel which is congruent with the path of the groove and has a cross section which is likewise rounded, in particular semicircular. In this case, it is to be assumed that the absence of the channel has less of an effect on the separation capacity than if the channel and groove are not uniformly congruent.

On the inner surfaces facing toward the groove, the support plate and the cover plate may be covered in a known way with a separation phase, in order in this way to effect the chromatographic separation. As an alternative or in addition, the support plate and the cover plate are porous on the inner surfaces facing toward the channel, the adsorption capacity of the inner surfaces and therefore their separation capacity being adjustable by means of the level of porosity.

To be able to set different separation-column lengths depending on the type of gases to be measured using the same separation-column unit, the support plate and/or the cover plate may contain continuous holes which run perpendicular to the plane of the plate and open into the groove at the ends of the groove and at predetermined intervening points. The holes in this case form the sample inlet and sample outlet for the intervening section of the separation column. However, instead of setting different separation-column lengths, it is preferably possible to change the flow velocity of the sample through the separation column which, as mentioned in the introduction, at relatively high velocities does not cause any significant deterioration to the separation capacity.

The groove may, for example, be designed in the form of a single spiral in the support plate. In this case, at least the inner end of the spiral leads outward through an opening in the support plate or cover plate. To avoid abrupt changes in cross section or flow diversions in the region of the sample inlet or outlet, the groove in the support plate preferably runs in the form of a double spiral, the groove emerging laterally from the support plate at both ends of the double spiral.

Alternatively, the groove runs in meandering form and emerges laterally from the support plate at both ends. Moreover, this has the advantage that, in addition to facilitating production, the path for the sample as it flows through the separation column does not cover a longer distance on one side of the groove than on the other side, as is the case with a groove in the shape of a spiral.

The groove may be formed in the support plate by anisotropic etching. This preferably takes place by dry etching, in particular reactive ion etching (IRE) in silicon. In this way, it is possible to form very steep groove flanks, so that the cross section of the groove and therefore of the separation column over the length of the cross section varies only to a negligible degree. Alternatively, the groove may be made in the carrier plate by means of a laser, which likewise results in very steep groove flanks. With a modified removal of material, for example a different etchant or etching process, such as isotropic etching, or a different laser wavelength, it is possible to form the base of the groove with a rounded, in particular semicircular cross section. This can also be achieved by forming the support plate from a first layer of material and a second layer of material, the thickness of the first layer of material corresponding to the depth of the groove which is to be formed and the second layer of material serving as a stopping layer for the groove-forming removal of material in the first layer of material. As a result, in particular a uniform depth of the groove over the length of the separation column to be formed is achieved. The base of the groove is preferably formed inside the second layer of material, which in terms of the material used is particularly suitable for forming recesses of semicircular cross section therein. A similar statement also applies to the cover plate, in which preferably a channel which is congruent with the path of the groove in the support plate and has a rounded, in particular semicircular cross section, is made. In this case, the base of the groove in the support plate and the channel in the cover plate can be formed by rinsing the groove with an etching solution when the cover plate is resting on the support plate, thus ensuring that the groove in the support plate and the channel in the cover plate are exactly congruent.

BRIEF DESCRIPTION OF THE DRAWINGS

To further explain the invention, reference is made in the following text to the figures of the drawing, in which, in detail.

DETAILED DESCRIPTION OF THE PREFERRED EMBODIMENTS

Figure 1:
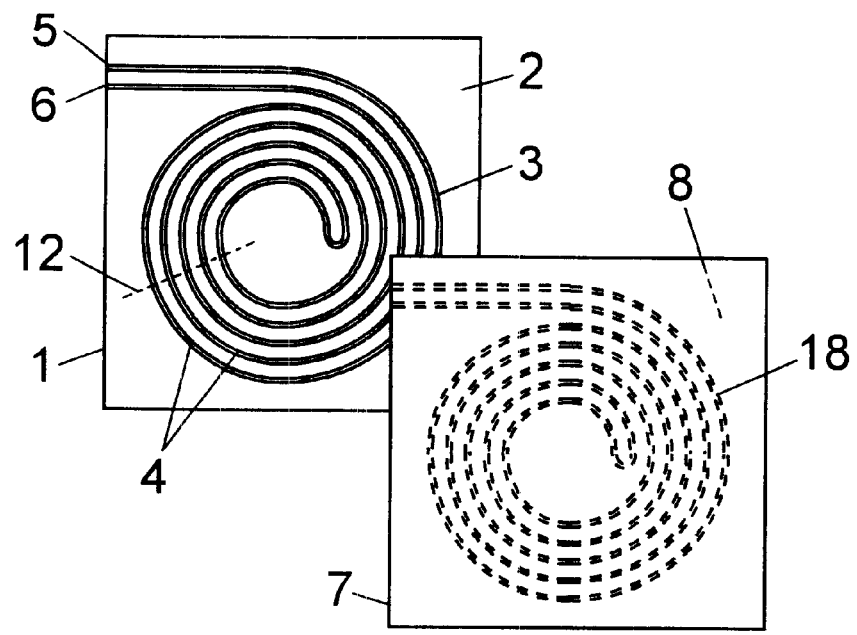
FIG. 1 shows a first exemplary embodiment of the separation-column unit according to the invention with support plate and cover plate detached from one another and a separation column running in the form of a double spiral.

FIG. 1 shows a support plate 1 in which a groove 3 has been made on one side 2. The groove 3 runs in a double spiral 4 and at its ends 5 and 6 emerges laterally from the support plate 1. For the sake of clarity of the drawing, only a few spiral turns are shown in this figure. To form a separation-column unit, the support plate 1 is covered, on its side 2, with a cover plate 7, the groove 3 and those regions of the cover plate 7 which cover it forming a capillary which, in order to form a separation column, is covered with a separation phase on its inner surfaces. The ends 5 and 6 of the groove 3 or the separation column which emerge laterally from the support plate 1 are used as sample inlet and outlet. On its side 8 which faces the support plate 1, the cover plate 7 may contain a channel 18 which is congruent with the groove 3.

Figure 2:
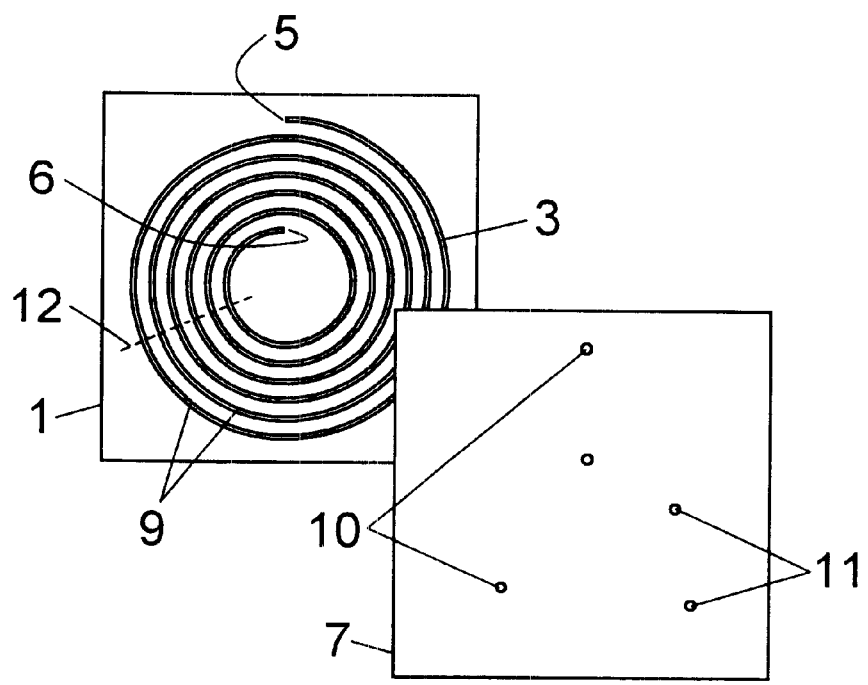
FIG. 2 shows a further exemplary embodiment of the separation-column unit with a separation column running in the form of a single spiral.

In the exemplary embodiment illustrated in FIG. 2, the groove 3 in the support plate 1 is designed in the form of a single spiral 9. To allow the intake or discharge of sample, the cover plate 7 contains two continuous holes 10 which run perpendicular to the plane of the plate and, after the two plates 1 and 7 have been connected, open out into the groove 3 at its ends 5 and 6. The cover plate 7 may contain further continuous holes 11 which open into the groove 3 at predetermined points and are used as sample inlet or outlet if only a partial length of the separation column is to be used; otherwise, the holes 11 are closed.

Figure 3:
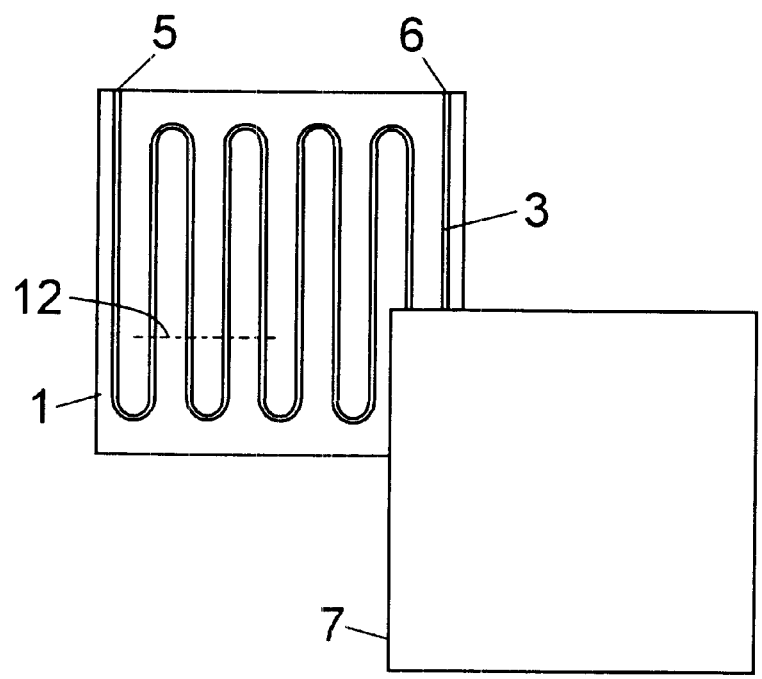
FIG.3 shows an additional exemplary embodiment of the separation-column unit with a separation column running in meandering form, and FIGS. 4 to 6 each show a partial cross section through the separation-column unit with the support plate and cover plate connected to one another and with different separation-column cross sections.

As shown in FIG. 3, the groove 3 may also be in meandering form in the support plate 1, in which case the groove 3 emerges laterally from the support plate 1 at its ends 5 and 6, as in the example shown in FIG. 1.

Figure 4:
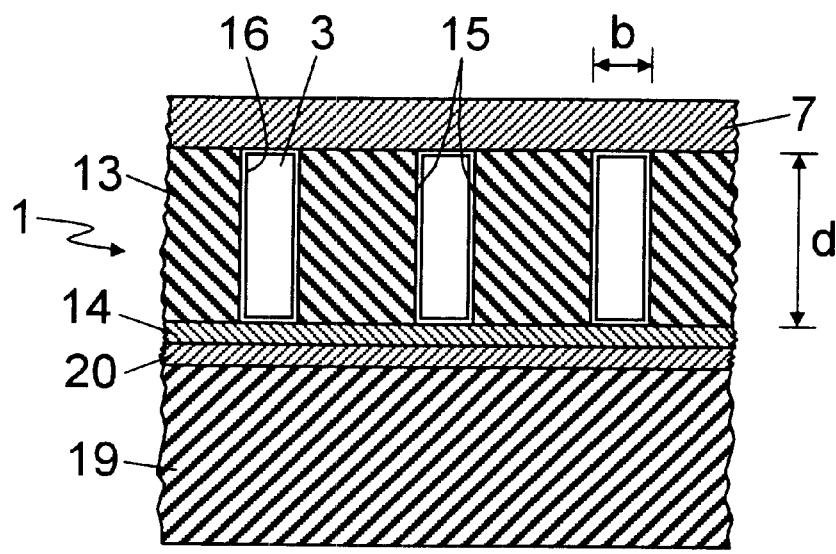

FIG. 4 shows a partial cross section through the assembled separation-column unit in accordance with FIGS.

1, 2 or 3, on line 12. The support plate 1 comprises two different layers of material 13 and 14, the groove 3 being formed in the layer of material 13 which adjoins the cover plate 7, with a depth d which is approximately four times greater than the width b of the groove 3. The first layer of material 13 consists of silicon with a thickness which corresponds to the depth d of the groove 3 which is to be formed, the groove 3 being made in this silicon with approximately perpendicular side flanks 15 by anisotropic etching. The second layer of material 14 serves as an etching stop and for this purpose consists of silica. In this case, the support plate 1 is, for example, a 600 μm thick silicon wafer, in which the second layer of material 14 comprising silica is formed with a thickness of typically 1 μm by oxidation. A further silica layer 20 is formed in the same way in a further silicon wafer 19, the two silicon wafers 1 and 19 subsequently being joined together on their sides which bear the silica layers 14, 20 by silicon fusion bonding. Then, the groove 3 is produced, with a width b of, for example, 150 μm, in the silicon wafer 1 by reactive ion etching.

In the exemplary embodiment shown, the inner surface of the groove 3 and of the cover plate 7 which covers it is covered by a liquid separation phase 16; the silicon of the first layer of material 13 may previously have been converted into silica in the region of the inner surface of the groove 3. Alternatively, the silicon of the first layer of material 13 may be converted into porous silicon in the region of the inner surface of the groove 3 and may be directly responsible for the separation phase function, in which case the porosity and therefore the adsorptive performance of the porous silicon on the side flanks 15 of the groove 3 are adjustable.

Figure 5:
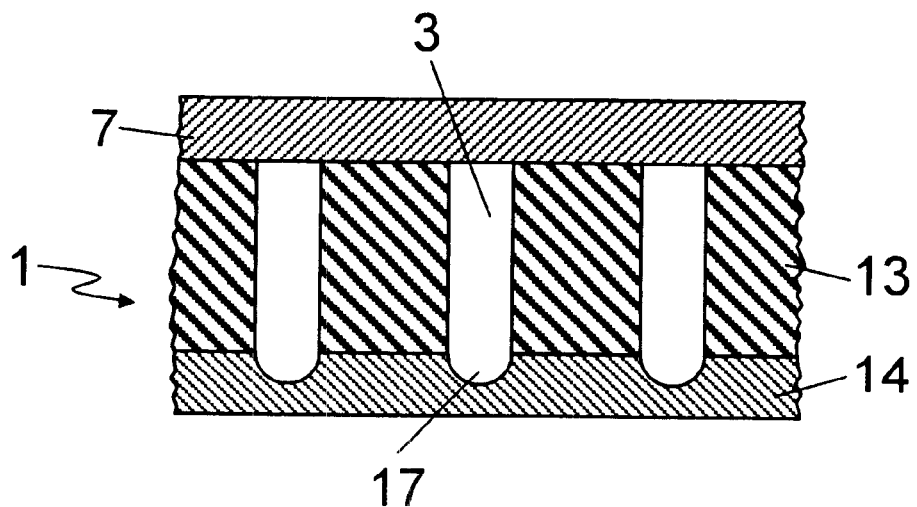

The exemplary embodiment of the separation-column unit according to the invention which is shown in FIG. 5 differs from that shown in FIG. 4 in that the base 17 of the groove 3 has a rounded, in this case semicircular cross section. To achieve this, the base 17 of the groove 3 is made in the second layer of material 14 by a further etching process which differs from the etching process used to form the side flanks 15 of the groove 3 in the first layer of material 13.

Figure 6:
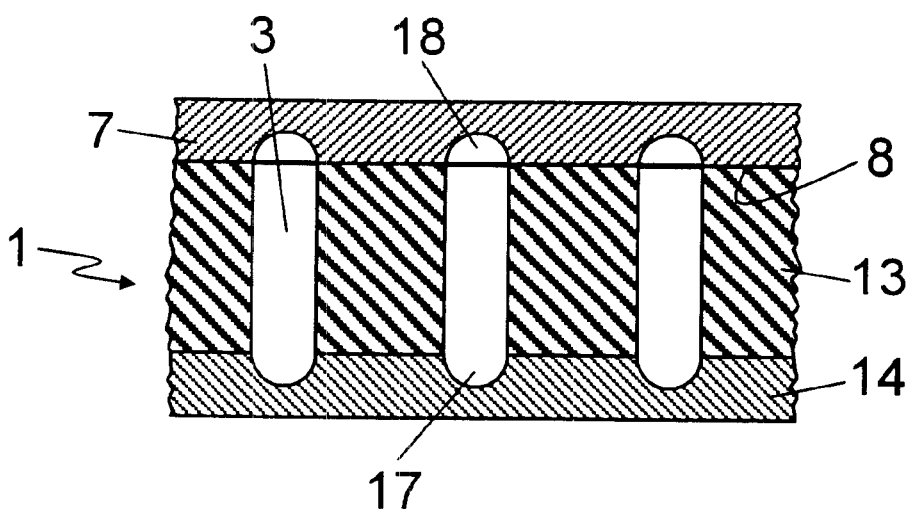

As the exemplary embodiment illustrated in FIG. 6 shows, it is additionally possible for the cover plate 7, on its side 8 which bears against the support plate 1, to contain a channel 18 which is likewise rounded in cross section and, as has already been shown in FIG. 1, runs congruently, in the form of a spiral, with the groove 3. To ensure congruence, the channel 18 and the rounded base 17 of the groove 3 are formed in one operation by rinsing the groove 3, with the cover plate 7 resting on top, with an etching solution.

What is claimed is:

1. A separation-column unit for a gas chromatograph comprising:
   a support plate, containing a groove running in a predetermined continuous line and covered by a cover plate on one side thereof, the depth (d) of the groove being greater than its width (b), wherein the groove in a region of its base, has a rounded cross section.

2. The separation-column unit as claimed in claim 1, wherein the cover plate, on its side facing toward the support plate, contains a channel which is congruent with a path of the groove and which has a rounded cross section.

3. The separation-column unit of claim 2, wherein the rounded cross section of the channel is semicircular.

4. The separation-column unit as claimed in claim 2, wherein the depth (d) of the groove is at least three times greater than its width (b).

5. The separation-column unit as claimed in claim 4, wherein the width (b) of the groove lies in a range between 100 and 150 μm and its depth (d) lies in a range between 500 and 600 μm.

6. The separation-column unit as claimed in claim 2, wherein the width (b) of the groove lies in a range between 100 and 150 μm and its depth (d) lies in a range between 500 and 600 μm.

7. The separation-column unit as claimed in claim 2, wherein the support plate and the cover plate are coated with a separation phase on the inner surfaces facing toward the groove.

8. The separation-column unit as claimed in claim 2, wherein the support plate and the cover plate are porous on the inner surfaces facing toward the groove.

9. The separation-column unit as claimed in claim 2, wherein at least one of the support plate and the cover plate contains continuous holes which run perpendicular to a plane of the plate and open into the groove at the ends of the groove and at predetermined intervening points.

10. The separation-column unit as claimed in claim 2, wherein the groove runs in the form of a double spiral and, at two ends of the double spiral, emerges laterally from the support plate.

11. The separation-column unit as claimed in claim 2, wherein the groove runs in meandering form and, at its two ends, emerges laterally from the support plate.

12. The separation-column unit as claimed in claim 1, wherein the depth (d) of the groove is at least three times greater than its width (b).

13. The separation-column unit as claimed in claim 12, wherein the width (b) of the groove lies in a range between 100 and 150 μm and its depth (d) lies in a range between 500 and 600 μm.

14. The separation-column unit as claimed in claim 12, wherein the support plate and the cover plate are coated with a separation phase on the inner surfaces facing toward the groove.

15. The separation-column unit as claimed in claim 12, wherein the support plate and the cover plate are porous on the inner surfaces facing toward the groove.

16. The separation-column unit as claimed in claim 12, wherein at least one of the support plate and the cover plate contains continuous holes which run perpendicular to a plane of the plate and open into the groove at the ends of the groove and at predetermined intervening points.

17. The separation-column unit as claimed in claim 12, wherein the groove runs in the form of a double spiral and, at two ends of the double spiral, emerges laterally from the support plate.

18. The separation-column unit as claimed in claim 12, wherein the groove runs in meandering form and, at its two ends, emerges laterally from the support plate.

19. The separation-column unit as claimed in claim 1, wherein the width (b) of the groove lies in a range between 100 and 150 μm and its depth (d) lies in a range between 500 and 600 μm.

20. The separation-column unit as claimed in claim 1, wherein the support plate and the cover plate are coated with a separation phase on the inner surfaces facing toward the groove.

21. The separation-column unit as claimed in claim 1, wherein the support plate and the cover plate are porous on the inner surfaces facing toward the groove.

22. The separation-column unit as claimed in claim 1, wherein at least one of the support plate and the cover plate contains continuous holes which run perpendicular a plane of the plate and open into the groove at the ends of the groove and at predetermined intervening points.

23. The separation-column unit as claimed in claim 1, wherein the groove runs in the form of a double spiral and, at two ends of the double spiral, emerges laterally from the support plate.

24. The separation-column unit as claimed in claim 1, wherein the groove runs in meandering form and, at its two ends, emerges laterally from the support plate.

25. The separation-column unit of claim 1, wherein the rounded cross section of the groove is semicircular.

26. A process for producing a separation-column unit for a gas chromatograph, comprising:

forming a groove, running along a predetermined continuous line with its depth (d) being greater than its width (b), on one side of a support plate of the separation-column unit by removal of material, with the support plate being covered on this side by a cover plate, wherein a base of the groove is formed by using a modified removal of material as compared to the formation of the rest of the groove, with a rounded cross section.

27. The process as claimed in claim 26, wherein the support plate is formed from a first layer of material and a second layer of material, a thickness of the first layer of material corresponding to the depth (d) of the groove which is to be formed, and the second layer of material serving as a stopping layer for the removal of material, which serves to form the groove in the first layer of material.

28. The process as claimed in claim 22, wherein the base of the groove is formed inside the second layer of material.

29. The process as claimed in claim 28, further comprising:

forming a channel congruent with a path of the groove and having a rounded cross section, in the cover plate.

30. The process as claimed in claim 28, wherein the groove is formed in the support anisotropic etching.

31. The process as claimed in claim 28, wherein the groove is formed in the support plate by means of a laser.

32. The process as claimed in claim 27, further comprising: forming a channel congruent with a path of the groove and having a rounded cross section, in the cover plate.

33. The process as claimed in claim 27, wherein the groove is formed in the support plate by an anisotropic etching.

34. The process as claimed in claim 27, wherein the groove is formed in the support plate by means of a laser.

35. The process as claimed in claim 26, further comprising:

forming a channel congruent with a path of the groove and having a rounded cross section, in the cover plate.

36. The process as claimed in claim 35, wherein the base of the groove in the carrier plate and the channel in the cover plate are formed by rinsing the groove with an etching solution with the cover plate resting on the support plate.

37. The process of claim 35, wherein the base of the groove is formed with a semicircular cross section.

38. The process as claimed in claim 26, wherein the groove is formed in the support plate by an anisotropic etching.

39. The process as claimed in claim 26, wherein the groove is formed in the support plate by means of a laser.

40. The process of claim 26, wherein the base of the groove is formed with a semicircular cross section.

* * * * *